(12) United States Patent
Li

(10) Patent No.: US 7,616,994 B2
(45) Date of Patent: Nov. 10, 2009

(54) FAST POST-ANTITACHYCARDIA PACING REDETECTION ALGORITHM

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 301 days.

(21) Appl. No.: 10/852,080

(22) Filed: May 24, 2004

(65) Prior Publication Data

US 2005/0261744 A1  Nov. 24, 2005

(51) Int. Cl.
*A61N 1/37* (2006.01)
*A61N 1/08* (2006.01)

(52) U.S. Cl. ............................................ 607/14; 607/4

(58) Field of Classification Search ................ 607/4, 607/14
See application file for complete search history.

(56) References Cited

U.S. PATENT DOCUMENTS

| | | | | |
|---|---|---|---|---|
| 4,202,340 | A | 5/1980 | Langer et al. ............... 128/419 |
| 4,559,947 | A * | 12/1985 | Renger et al. .................. 607/9 |
| 4,809,697 | A * | 3/1989 | Causey et al. ................. 607/31 |
| 4,825,870 | A | 5/1989 | Mann et al. ........... 128/419 PG |
| 4,830,006 | A | 5/1989 | Haluska et al. ................. 607/4 |
| 4,974,589 | A | 12/1990 | Sholder ................ 128/419 PG |
| 5,103,820 | A | 4/1992 | Markowitz .......... 128/419 OPG |
| 5,129,393 | A | 7/1992 | Brumwell ............. 128/419 PG |
| 5,144,949 | A | 9/1992 | Olson ................... 128/419 PG |
| 5,161,529 | A | 11/1992 | Stotts et al. ................. 128/419 |
| 5,188,105 | A * | 2/1993 | Keimel .......................... 607/5 |
| 5,193,535 | A | 3/1993 | Bardy et al. ............ 128/419 D |
| 5,193,550 | A | 3/1993 | Duffin ......................... 129/697 |
| 5,205,283 | A | 4/1993 | Olson ................... 128/419 PG |
| 5,209,229 | A | 5/1993 | Gilli ....................... 128/419 D |
| 5,222,493 | A | 6/1993 | Sholder ........................ 607/27 |
| 5,224,475 | A | 7/1993 | Berg et al. .............. 128/419 D |

(Continued)

FOREIGN PATENT DOCUMENTS

EP  0684011 A1  5/1995

(Continued)

OTHER PUBLICATIONS

"AICD System Guide, Model 1900, Ventak Prizm", *Guidant Corporation*, (Apr. 1, 2002), 306 pgs.

(Continued)

*Primary Examiner*—Carl H. Layno
*Assistant Examiner*—Tammie K. Heller
(74) *Attorney, Agent, or Firm*—Schwegman, Lundberg & Woessner, P.A.

(57) ABSTRACT

A method comprising detecting a ventricular tachycardia heart rhythm in a patient, providing anti-tachycardia pacing (ATP) therapy to the patient in response to the ventricular tachycardia heart rhythm, waiting a first time duration after the ATP therapy ends, and monitoring ventricular depolarizations after the first time duration has elapsed. The monitoring includes measuring time intervals between the ventricular depolarizations, and if a consecutive number of the intervals between the ventricular depolarizations are shorter than a first threshold interval value, then the method includes deeming that the ventricular tachycardia rhythm persists. Otherwise, if a fraction of the intervals between the ventricular depolarizations are shorter than a second threshold interval value, then the method includes deeming that the ventricular tachycardia heart rhythm persists, and otherwise deeming that the ventricular tachycardia rhythm is converted.

25 Claims, 5 Drawing Sheets

U.S. PATENT DOCUMENTS

| | | | |
|---|---|---|---|
| 5,251,624 A | 10/1993 | Bocek et al. | 607/6 |
| 5,257,621 A | 11/1993 | Bardy et al. | 607/5 |
| 5,273,035 A | 12/1993 | Markowitz et al. | 607/14 |
| 5,311,874 A | 5/1994 | Baumann et al. | 128/705 |
| 5,312,445 A | 5/1994 | Nappholz et al. | 607/9 |
| 5,324,310 A | 6/1994 | Greeninger et al. | 607/28 |
| 5,327,900 A | 7/1994 | Mason et al. | 128/705 |
| 5,330,505 A | 7/1994 | Cohen | 607/6 |
| 5,330,508 A | 7/1994 | Gunderson | 607/14 |
| 5,342,402 A | 8/1994 | Olson et al. | 607/5 |
| 5,342,405 A | 8/1994 | Duncan | 607/17 |
| 5,350,410 A | 9/1994 | Kleks et al. | 607/28 |
| 5,354,316 A | 10/1994 | Keimel | 607/15 |
| 5,366,486 A | 11/1994 | Zipes et al. | 607/5 |
| 5,370,667 A | 12/1994 | Alt | 607/19 |
| 5,379,776 A | 1/1995 | Murphy et al. | 128/705 |
| 5,383,910 A | 1/1995 | den Dulk | 607/14 |
| 5,400,796 A | 3/1995 | Wecke | 128/705 |
| 5,403,352 A | 4/1995 | Rossing | 607/4 |
| 5,458,619 A | 10/1995 | Olson | |
| 5,458,622 A | 10/1995 | Alt | 607/15 |
| 5,472,453 A | 12/1995 | Alt | 607/4 |
| 5,534,016 A | 7/1996 | Boute | 607/9 |
| 5,545,186 A * | 8/1996 | Olson et al. | 607/14 |
| 5,548,619 A | 8/1996 | Horiike et al. | 375/344 |
| 5,587,970 A | 12/1996 | Greenwood | 368/10 |
| 5,591,214 A | 1/1997 | Lu | 607/9 |
| 5,658,320 A | 8/1997 | Betzold et al. | 607/14 |
| 5,662,688 A | 9/1997 | Haefner et al. | 607/5 |
| 5,683,424 A | 11/1997 | Brown et al. | 607/5 |
| 5,683,431 A | 11/1997 | Wang | 607/28 |
| 5,713,932 A | 2/1998 | Gillberg et al. | 607/27 |
| 5,776,167 A | 7/1998 | Levine et al. | 607/9 |
| 5,836,971 A | 11/1998 | Starkweather | 607/4 |
| 5,846,263 A | 12/1998 | Peterson et al. | 607/14 |
| 5,855,593 A | 1/1999 | Olson et al. | 607/9 |
| 5,857,977 A | 1/1999 | Caswell et al. | 600/518 |
| 5,868,793 A | 2/1999 | Nitzsche et al. | 607/5 |
| 5,871,512 A | 2/1999 | Hemming et al. | 607/28 |
| 5,873,897 A | 2/1999 | Armstrong et al. | 607/14 |
| 5,891,170 A | 4/1999 | Nitzsche et al. | 607/4 |
| 5,893,882 A | 4/1999 | Peterson et al. | 607/14 |
| 5,978,700 A | 11/1999 | Nigam | 600/518 |
| 5,978,707 A | 11/1999 | Krig et al. | 607/14 |
| 5,999,854 A | 12/1999 | Deno et al. | 607/18 |
| 6,091,988 A | 7/2000 | Warman et al. | 607/5 |
| 6,101,414 A | 8/2000 | Kroll | 607/14 |
| 6,128,529 A | 10/2000 | Esler | 607/4 |
| 6,137,308 A | 10/2000 | Nayak | 326/39 |
| 6,151,524 A | 11/2000 | Krig et al. | 607/14 |
| 6,167,308 A | 12/2000 | DeGroot | 607/14 |
| 6,192,275 B1 | 2/2001 | Zhu et al. | 607/28 |
| 6,230,055 B1 | 5/2001 | Sun et al. | 607/5 |
| 6,317,632 B1 | 11/2001 | Krig et al. | 607/14 |
| 6,400,986 B1 | 6/2002 | Sun et al. | 607/14 |
| 6,449,503 B1 | 9/2002 | Hsu | |
| 6,456,871 B1 | 9/2002 | Hsu et al. | 600/518 |
| 6,459,932 B1 | 10/2002 | Mehra | 607/5 |
| 6,477,420 B1 | 11/2002 | Struble et al. | 607/14 |
| 6,477,422 B1 | 11/2002 | Splett | 607/28 |
| 6,480,734 B1 | 11/2002 | Zhang et al. | |
| 6,493,579 B1 | 12/2002 | Gilkerson et al. | 607/5 |
| 6,522,925 B1 | 2/2003 | Gilkerson et al. | 607/30 |
| 6,643,547 B2 | 11/2003 | Kim | 607/14 |
| 6,658,286 B2 | 12/2003 | Seim | 600/516 |
| 6,671,548 B1 * | 12/2003 | Mouchawar et al. | 607/14 |
| 6,748,269 B2 | 6/2004 | Thompson et al. | 607/4 |
| 6,775,572 B2 | 8/2004 | Zhu et al. | 607/14 |
| 6,801,806 B2 | 10/2004 | Sun et al. | 607/14 |
| 6,889,081 B2 | 5/2005 | Hsu | |
| 7,043,302 B1 | 5/2006 | Florio et al. | |
| 7,103,411 B1 | 9/2006 | Park | |
| 7,113,824 B2 | 9/2006 | Krig et al. | |
| 7,142,911 B2 * | 11/2006 | Boileau et al. | 607/3 |
| 7,174,209 B2 | 2/2007 | Thompson et al. | |
| 7,277,750 B2 | 10/2007 | Perschbacher et al. | |
| 2002/0198461 A1 | 12/2002 | Hsu et al. | 600/518 |
| 2003/0083704 A1* | 5/2003 | Baker et al. | 607/14 |
| 2003/0120315 A1 | 6/2003 | Spinelli et al. | 607/14 |
| 2004/0093037 A1* | 5/2004 | Henry | 607/14 |
| 2004/0254613 A1 | 12/2004 | Ostroff et al. | |
| 2005/0010122 A1* | 1/2005 | Nearing et al. | 600/509 |
| 2005/0137626 A1* | 6/2005 | Pastore et al. | 607/3 |
| 2005/0149135 A1 | 7/2005 | Krig et al. | |
| 2005/0192505 A1 | 9/2005 | Ostroff et al. | |

FOREIGN PATENT DOCUMENTS

| | | |
|---|---|---|
| EP | 0744190 A2 | 5/1996 |
| WO | WO-98/40122 A1 | 9/1998 |

OTHER PUBLICATIONS

Berul, C I., "Comparison of initial detection and redetection of ventricular fibrillation in a transvenous defibrillator system with automatic gain control", *Journal of the American College of Cardiology*, 25(2), (Feb. 1995), 431-6.

Fries, R , et al., "Antitachycardia pacing in patients with implantable cardioverter defibrillators: how many attempts are useful", *Pacing and Clinical Electrophysiology*, 20(1 Pt 2), (Jan. 1997), 198-202.

Kim, J., "Method and Device for Sensing Atrial Depolarizations During Ventricular Tachycardia", U.S. Appl. No. 10/700,373, filed Nov. 3, 2003 17 Pages.

Lecarpentier, G L., "Differentiation of sinus tachycardia from ventricular tachycardia with 1:1 ventriculoatrial conduction in dual chamber implantable cardioverter defibrillators: feasibility of a criterion based on the atrioventricular interval", *Pacing Clin Electrophysiol.*, 17(11 Pt 1), (Nov. 1994),1818-31.

Miller, R E., et al., "Description and evaluation of the Res-Q Arrhythmia Control Device.", *Journal of cardiovascular electrophysiology*, 6(2), (Feb. 1995), 147-61.

Nair, M , "Automatic arrhythmia identification using analysis of the atrioventricular association. Application to a new generation of implantable defibrillators. Participating Centers of the Automatic Recognition of Arrhythmia Study Group.", *Circulation*, 95(4), (Feb. 1997),967-73.

Olson, W. , "Safety Margins for Sensing and Detection: Programming Tradeoffs", *Implantable Cardioverter Defibrillator Therapy. The Engineering Clinical Interface (Development in Cardiovascular Medicine*, 188) By Mark W. Kroll & Michael H. Lehmann, Shepard & Epstein,(1996),388-420.

Stevenson, S A., "A:V = 1:1 cardiac arrhythmia detection by VA interval analysis", *J Electrocardiol.*, 29 Suppl, (1996), 198-201.

Thompson, J. , et al., "Algorithm for Discrimination of 1:1 Tachycardias", U.S. Appl. No. 10/862,779, filed Jun. 7, 2004, 33 Pages.

Thompson, Julie A., "An Improved Method of Discriminationof 1:1 Tachycardias using a Variance Based Model of Electrical Conduction of the Heart", *Ph.D. Dissertation*, University of Michigan, (2000),194.

Thompson, Julie , "Improved Differentiation of 1:1 Tachycardias in Dual-Chamber ICDs Using Interval Variability", *North American Society of Pacing and Electrophysiology* (NASPE) Conference held in Boston, MA on May 4, 2001., 14.

Thompson, J , "Recognition of ventricular tachycardia with 1:1 retrograde atrial activation: A new algorithm for implantable cardioverter defibrillators", *Proceedings of the 19th Annual International Conference of the IEEE Engineering in Medicine and Biology Society. 'Magnificent Milestones and Emerging Opportunities in Medical Engineering'*, pt. 1, vol. 1, (1997),393-4.

Thompson, J. , "Template Based AV/VA Interval Comparison for the Discrimination of Cardiac Arrhythmia", U.S. Appl. No. 10/844,475, filed May 12, 2004, 33 Pages.

Thompson, J A., "Ventriculoatrial conduction metrics for classification of ventricular tachycardia with 1:1 retrograde condition in dual-chamber sensing implantable cardioverter defibrillators", *J Electrocardiol.*, 31 Suppl, (1998), 152-6.

Throne, R D., "Discrimination of retrograde from anterograde atrial activation using intracardiac electrogram waveform analysis", *Pacing Clin Electrophysiol.*,12(10), (Oct. 1989), 1622-30.

Wathen, Mark S., et al., "Shock reduction using antitachycardia pacing for spontaneous rapid ventricular tachycardia in patients with coronary artery disease", *Circulation*, 104(7), (Aug. 14, 2001),796-801.

Weber, Max M., et al., "Antitachycardia pacing for rapid VT during ICD charging: a method to prevent ICD shocks", *Pacing and Clinical Electrophysiology*, 24(3), (Mar. 2001),345-351.

Wietholt, D , et al., "Clinical experience with antitachycardia pacing and improved detection algorithms in a new implantable cardioverter-defibrillator", *Journal of the American College of Cardiology*, 21(4), (Mar. 15, 1993),885-94.

Zhang, Y. , "ATP Pacing With Entrainment Monitoring", U.S. Appl. No. 10/835,078, filed Apr. 29, 2004, 18 Pages.

Zhang, Y. , "ATP Therapy for Tachyarrhythmias in VF Zone", U.S. Appl. No. 10/909,740, filed Aug. 2, 2004, 17 Pages.

Zhang, Y , "Selective Chamber ATP Pacing", U.S. Appl. No. 10/858,564, filed Jun. 1, 2004, 16 Pages.

Zhu, Q. , et al., "Method and System for Automatic Anti-Tachycardia Pacing", U.S. Appl. No. 10/914,495, filed Aug. 9, 2004, 20 Pages.

"U.S. Appl. No. 08/947,256 Non-Final Office Action mailed Nov. 30, 1998", 12 Pages.

"U.S. Appl. No. 08/947,256 Non-Final Office Action mailed Jun. 5, 1998", 9 Pages.

"U.S. Appl. No. 08/947,256 Notice of Allowance mailed May 13, 1999", 3 Pages.

"U.S. Appl. No. 08/947,256 Response filed Oct. 5, 1998 to Non-Final Office Action mailed Jun. 5, 1998", 15 pages.

"U.S. Appl. No. 08/947,256 Response filed Mar. 30, 1999 to Non-Final Office Action mailed Nov. 30, 1998", 11 Pages.

"U.S. Appl. No. 09/376,245 Non-Final Office Action mailed Jan. 28, 2000", 8 Pages.

"U.S. Appl. No. 09/376,245 Non-Final Office Action mailed Feb. 23, 2000", 7 Pages.

"U.S. Appl. No. 09/376,245 Notice of Allowance mailed Jul. 3, 2000", 3 pages.

"U.S. Appl. No. 09/376,245 Response filed Feb. 11, 2000 to Non-Final Office Action mailed Jan. 28, 2000", 7 Pages.

"U.S. Appl. No. 09/376,245 Response filed May 23, 2000 to Non-Final Office Action mailed Feb. 23, 2000", 6 Pages.

"U.S. Appl. No. 09/686,585 Non-Final Office Action Mailed Jan. 31, 2001", 6 pages.

"U.S. Appl. No. 09/686,585 Notice of Allowance mailed Jun. 15, 2001", 4 pages.

"U.S. Appl. No. 09/686,585 Response filed Apr. 26, 2001 to Non-Final Office Action mailed Jan. 31, 2001", 7 pages.

"U.S. Appl. No. 10/008,367 Prosecution History as of Oct. 28, 2007", 96 pages.

"U.S. Appl. No. 11/073,818 Prosecution History as of Oct. 28, 2007", 61 pages.

* cited by examiner

FAST POST-ANTITACHYCARDIA PACING REDETECTION ALGORITHM

TECHNICAL FIELD

The field generally relates to implantable medical devices and, in particular, but not by way of limitation, to systems and methods for detecting ventricular tachycardia heart rhythms.

BACKGROUND ART

Implantable medical devices (IMDs) are devices designed to be implanted into a patient. Some examples of these devices include cardiac rhythm management devices such as implantable pacemakers and implantable cardioverter defibrillators (ICDs). The devices are used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient. Some IMDs detect tachyarrhythmia in a patient's heart. It is important to quickly and correctly detect tachyarrhythmia.

SUMMARY

Systems and methods are provided for detecting tachycardia heart rhythms. In one system example, the system includes an implantable medical device (IMD) comprising a signal sensing circuit coupled to at least one electrode where the electrode is located to sense a cardiac signal of a ventricle of a heart of a patient, a therapy circuit, a timer circuit, and a controller coupled to the signal sensing circuit, the timer circuit, and the therapy circuit. The controller is operable in detecting ventricular tachycardia heart rhythm from the cardiac signal initiating anti-tachycardia pacing (ATP) therapy to the patient in response to the ventricular tachycardia heart rhythm, measuring time intervals between ventricular depolarizations after providing ATP therapy, and in comparing the intervals to a threshold interval value. If a consecutive number of the intervals are shorter than the threshold interval value, then the controller deems that the ventricular tachycardia rhythm persists. Otherwise, if a fraction of the intervals are shorter than the threshold interval value, then the controller deems that the ventricular tachycardia heart rhythm persists, otherwise the controller deems that the ventricular tachycardia heart rhythm is converted.

In one method example, the method comprises detecting a ventricular tachycardia heart rhythm in a patient, providing anti-tachycardia pacing (ATP) therapy to the patient in response to the ventricular tachycardia heart rhythm, waiting a first time duration after the ATP therapy ends, and monitoring ventricular depolarizations after the first time duration has elapsed. The monitoring includes measuring time intervals between the ventricular depolarizations, and if a consecutive number of the intervals between the ventricular depolarizations are shorter than a first threshold interval value, then the method includes deeming that the ventricular tachycardia rhythm persists. Otherwise, if a fraction of the intervals between the ventricular depolarizations are shorter than a second threshold interval value, then the method includes deeming that the ventricular tachycardia heart rhythm persists and otherwise deeming that the ventricular tachycardia rhythm is converted.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The present application discusses, among other things, systems and methods for detecting ventricular tachyarrhythmia. When ventricular tachycardia is detected, implantable medical devices (IMDs) are designed to provide therapy to the patient. Some IMDs, such as implantable cardioverter defibrillators (ICDs), treat tachycardia by delivering a high energy electrical shock to the heart. Other IMDs provide anti-tachycardia pacing (ATP). ATP uses lower energy pacing energy to establish a regular rhythm in a heart. This allows the tachycardia to be converted to a normal heart rhythm without exposing the patient to high energy defibrillation therapy that can be painful to the patient.

Some IMDs are able to provide both ATP and defibrillation. When tachycardia is detected, the device may try to convert the arrhythmia with ATP before resorting to high energy defibrillation. After delivery of ATP therapy, it is important to quickly determine if the tachycardia still persists or whether the tachycardia has been converted to a normal heart rhythm.

Figure 1:
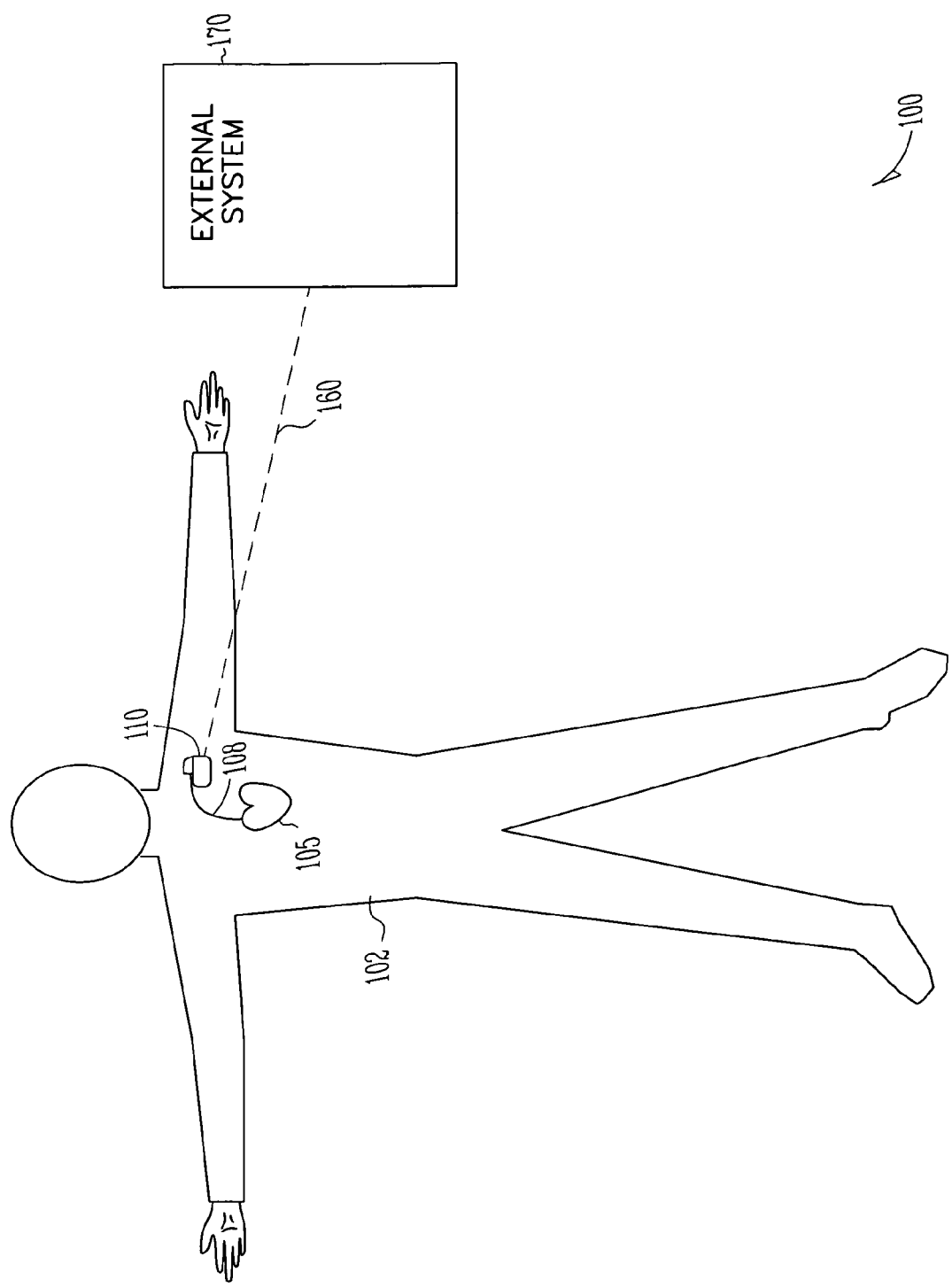
FIG. 1 illustrates an embodiment of a system that uses an implantable medical device.

FIG. 1 illustrates an embodiment of a system 100 that uses an implantable medical device (IMD) 110. The system 100 shown is one embodiment of portions of a system 100 used to treat a cardiac arrhythmia. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. Other examples include IMDs that deliver a drug therapy to a patient in response to ventricular tachyarrhythmia. System 100 also includes an IMD programmer or other external system 170 that provides wireless communication signals 160 to communicate with the IMD 110, such as by using telemetry or radio frequency (RF) signals.

Cardiac lead 108 includes a proximal end that is coupled to IMD 110 and a distal end, coupled by an electrode or electrodes to one or more portions of a heart 105. The electrodes are for delivering atrial and/or ventricular cardioversion/defibrillation and/or pacing or resynchronization therapy to the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105.

Figure 2:
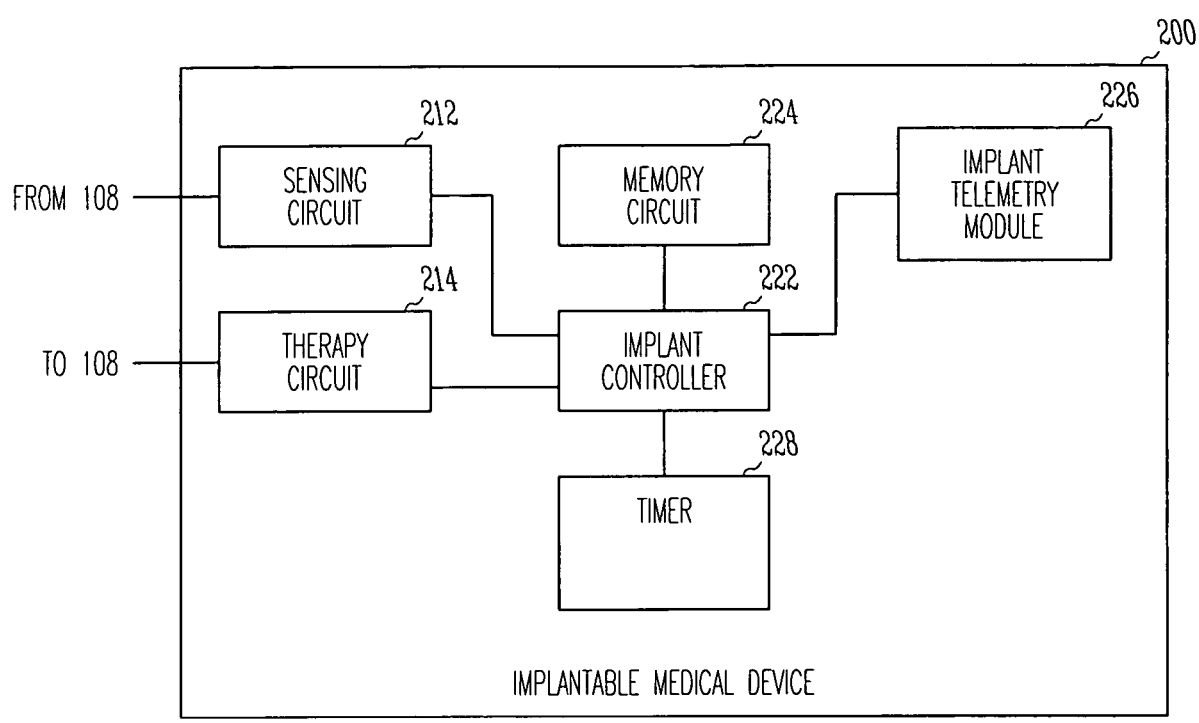
FIG. 2 is a block diagram of an implantable medical device (IMD).

FIG. 2 is a block diagram of an implantable medical device (IMD) 200 used in a system for detecting ventricular tachyarrhythmia. The IMD 200 includes a signal sensing circuit 212 to sense electrical signals on the lead or leads 108 and electrodes. To sense the electrical signals, the sensing circuit 212 includes sense amplifier circuits (not shown). The IMD 200 includes a therapy circuit 214 to deliver electrical therapy to heart 105 through the lead or leads 108 and electrodes. The IMD 200 includes a timer circuit 228 that is operable to determine time durations between events, and a controller 222 coupled to the signal sensing circuit, the timer circuit, and the therapy circuit. The controller 222 is operable to detect a ventricular tachycardia heart rhythm from the cardiac signal from an electrical signal provided by the sensing circuit 212 and initiate anti-tachycardia pacing (ATP) therapy to the patient using the therapy circuit 214. The efficacy of the ATP therapy then needs to be determined.

After providing ATP therapy, the controller 222 is operable to measure time intervals between ventricular depolarizations using the timer circuit 228. The controller 222 compares the measured time intervals to a threshold interval value and if a consecutive number of the intervals are shorter than the threshold interval value, the controller 222 then deems that the ventricular tachycardia rhythm persists. The threshold interval value and the required number of consecutive intervals are programmable values. The number of consecutive intervals is determined in part by how quickly it is desired to redetect the arrhythmia. If a consecutive number of the intervals are not shorter than the threshold interval value, the controller 222 then determines if a predetermined fraction of the intervals are shorter than the threshold interval value. If so, the controller 222 then deems that the ventricular tachycardia heart rhythm persists. The predetermined fraction of the intervals is a programmable value. In one embodiment, the controller 222 counts consecutive depolarization intervals, such as for example ten depolarizations. The controller 222 also counts how many of the depolarizations are shorter than the threshold. If a number of the ten depolarizations (such as for example six depolarizations corresponding to a fraction of sixty percent) are shorter than the threshold interval value, then the controller 222 deems that the ventricular tachycardia heart rhythm persists. If a fraction of the intervals is not shorter than the threshold interval value, then the controller 222 deems that the ventricular tachycardia heart rhythm is converted into a regular heart rhythm.

In another embodiment the IMD 200 includes an atrial signal sensing circuit coupled to at least one second electrode and the controller 222. The at least one second electrode is located to sense a cardiac signal of an atrium of the heart. In the embodiment, in addition to measuring the intervals between ventricular depolarizations, the controller 222 is further operable to measure both a ventricular depolarization rate and an atrial depolarization rate for the patient. If the ventricular depolarization rate exceeds the atrial depolarization rate by a threshold rate difference value, the controller 222 then deems that the ventricular tachycardia heart rhythm persists; otherwise the controller deems that the ventricular tachycardia rhythm is converted.

In yet another embodiment, the controller 222 is operable to time a programmable wait duration after providing ATP therapy and before measuring the time intervals. In yet another embodiment, the controller 222 is operable to time a programmable redetection duration during which the controller measures the time intervals between the ventricular depolarizations. In the embodiment, the controller 222 deems the ventricular tachycardia heart rhythm to be converted to a regular rhythm if the redetection duration elapses without deeming that the ventricular tachycardia heart rhythm persisted.

In other embodiments, the IMD 200 provides therapy if it is deemed that the ventricular tachycardia heart rhythm persists. In one embodiment the therapy circuit 214 includes a pacing therapy circuit and the IMD 200 provides further ATP therapy. In another embodiment, the therapy circuit 214 includes a defibrillation therapy circuit and the IMD 200 provides defibrillation therapy if the ventricular tachycardia heart rhythm is deemed to persist. In yet another embodiment, the therapy circuit 214 includes a combination of pacing and defibrillation therapy circuits. In an embodiment having both having pacing and defibrillation circuits, the IMD 200 provides ATP therapy while the defibrillation therapy circuit is charging, and wherein the controller 222 is operable to determine if the ventricular tachycardia rhythm is converted while the defibrillation therapy circuit is charging. In another embodiment, the controller 222 is operable to abort the charging of the defibrillation therapy circuit if the ventricular tachycardia rhythm is deemed converted.

In another embodiment, the therapy circuit includes a drug therapy circuit and the implantable medical device provides drug therapy if the ventricular tachycardia heart rhythm is deemed to persist. In another embodiment, the IMD 222 includes combinations of pacing, defibrillation, and drug therapy circuits and provides one or a combination of pacing, defibrillation, and drug therapy to the patient. In one embodiment, the drug is delivered to convert the tachycardia. In another embodiment, the drug is delivered in combination with defibrillation therapy to provide pain relief.

In another embodiment, the IMD 200 includes a memory 224 coupled to the controller 222. The controller 222 is operable to store patient information about whether a ventricular tachycardia heart rhythm was converted. In yet another embodiment, the system to detect ventricular tachyarrhythmia includes the IMD 200 and an external system (170 in FIG. 1) operable to communicate with the IMD 200. The IMD 200 is operable to send the patient information to the external system. The external system includes a display to display patient information related to at least one redetection duration and whether a ventricular tachycardia heart rhythm was converted to a regular rhythm during the redetection duration. In another embodiment, the patient information includes a histogram of patient information related to at least one redetection duration and whether a ventricular tachycardia heart rhythm was converted. In yet another embodiment, the external system is operable to communicate with a computer network. For example, the computer network could include the internet and/or a hospital computer network.

Figure 3A:
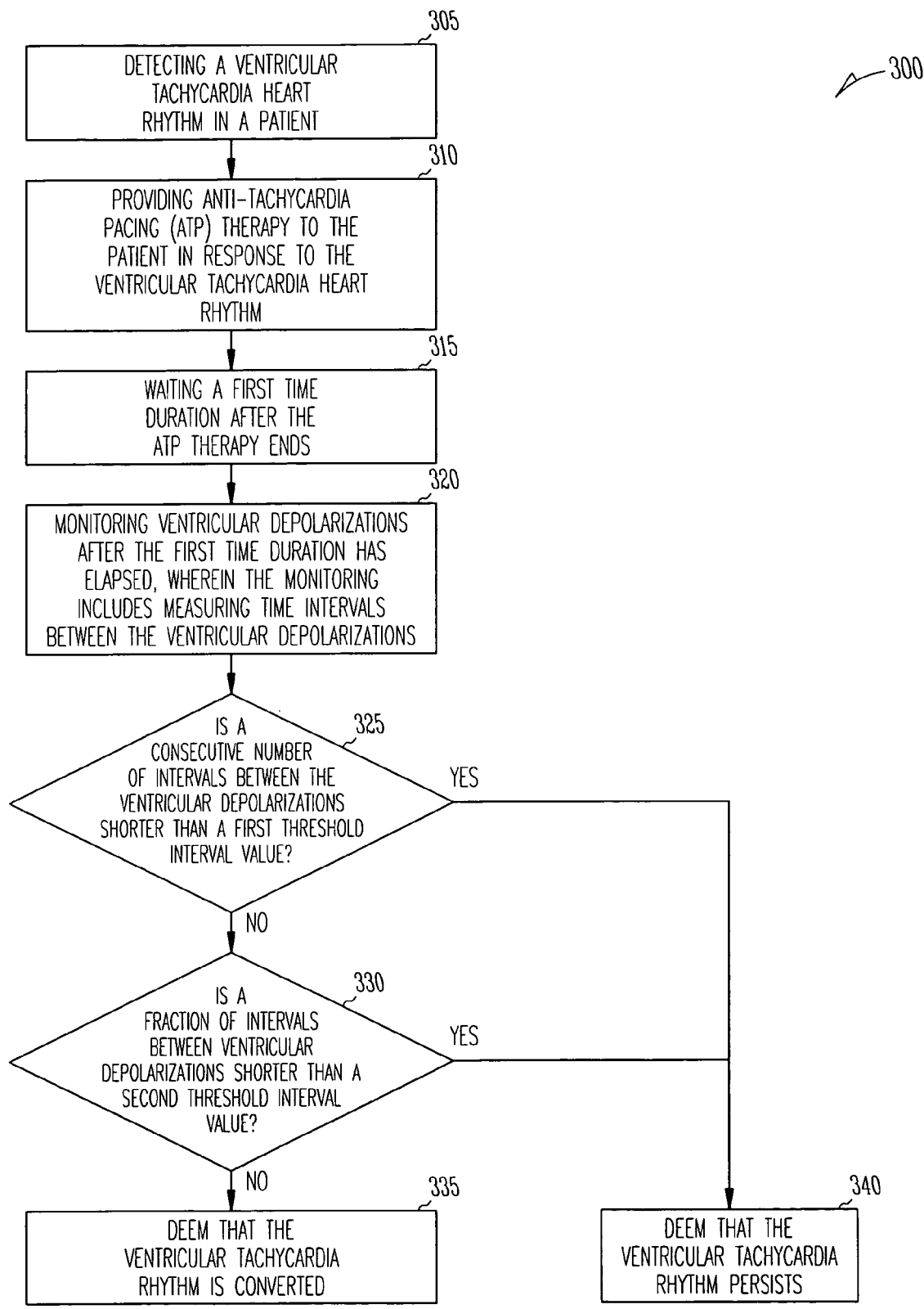
FIGS. 3A and 3B are block diagrams illustrating a method of re-detecting ventricular tachycardia heart rhythm.

FIG. 3A shows an embodiment of a method 300 of redetecting ventricular tachycardia heart rhythm. At 305, a ventricular tachycardia heart rhythm is detected in a patient. At 310, anti-tachycardia pacing (ATP) therapy is provided to the patient in response to the ventricular tachycardia heart rhythm. In one example, the tachycardia is detected by monitoring an electrical signal from a patient's heart and the therapy is provided with a therapy circuit of an IMD. At 315, a first duration is timed after the ATP therapy ends. At 320, ventricular depolarizations are monitored after the first time duration has elapsed. The monitoring includes measuring time intervals between the ventricular depolarizations. At

325, if a consecutive number of the intervals between the ventricular depolarizations are shorter than a first threshold interval value, then at 340 it is deemed that the ventricular tachycardia rhythm persists. Otherwise, at 330, if a fraction of the intervals between the ventricular depolarizations are shorter than a second threshold interval value, then at 340, it is deemed that the ventricular tachycardia heart rhythm persists; otherwise, at 335 it is deemed that the ventricular tachycardia rhythm is converted.

In another embodiment of the method 300, the first and second threshold interval values are the same value. In yet another embodiment, a second duration time called a redetection duration time is timed after ATP therapy ends. The redetection duration time includes the time that the ventricular depolarizations are monitored. In the embodiment, the ventricular tachycardia heart rhythm is deemed converted to a regular rhythm if the redetection duration elapses without deeming that the ventricular tachycardia heart rhythm persisted. The redetection duration time may include the first duration time or it may begin after the first duration time ends.

An embodiment of the redetection method shown in FIG. 3A was applied to a database containing data collected from one hundred seventeen post-ATP episodes. The episodes were recorded from forty patients. The purpose of applying the method to the database was to determine how accurate the method was in detecting a persistent ventricular tachycardia (i.e. the method's sensitivity) and in correctly detecting that a ventricular tachycardia was converted (i.e. the method's specificity). To determine the sensitivity and specificity, the results were compared to an expert's annotations of the episodes.

For the embodiment of the method applied, the first duration time was two seconds. The first and second threshold interval values were the same value and based on a 165 beat-per-minute (bpm) ventricular rate. The consecutive number of intervals that had to be shorter than the threshold interval before deeming ventricular tachycardia to persist was three, and the fraction of intervals that had to be shorter than the threshold interval before deeming ventricular tachycardia to persist was fifty percent. The resulting sensitivities and specificities that were determined while varying the redetection duration time are indicated below in Table 1. The redetection duration times indicated include the first duration time.

TABLE 1

Redetection Specificity and Sensitivity Results without Rate Check

| Redetection Duration Time (sec) | Sensitivity (%) | Specificity (%) |
|---|---|---|
| 5 | 89.7 | 93.2 |
| 4.5 | 86.2 | 89.8 |
| 4 | 93.1 | 88.6 |
| 3.5 | 82.8 | 86.4 |
| 3 | 93.1 | 81.8 |

The results show that ventricular tachycardia can be redetected using the method in three seconds.

Figure 3B:
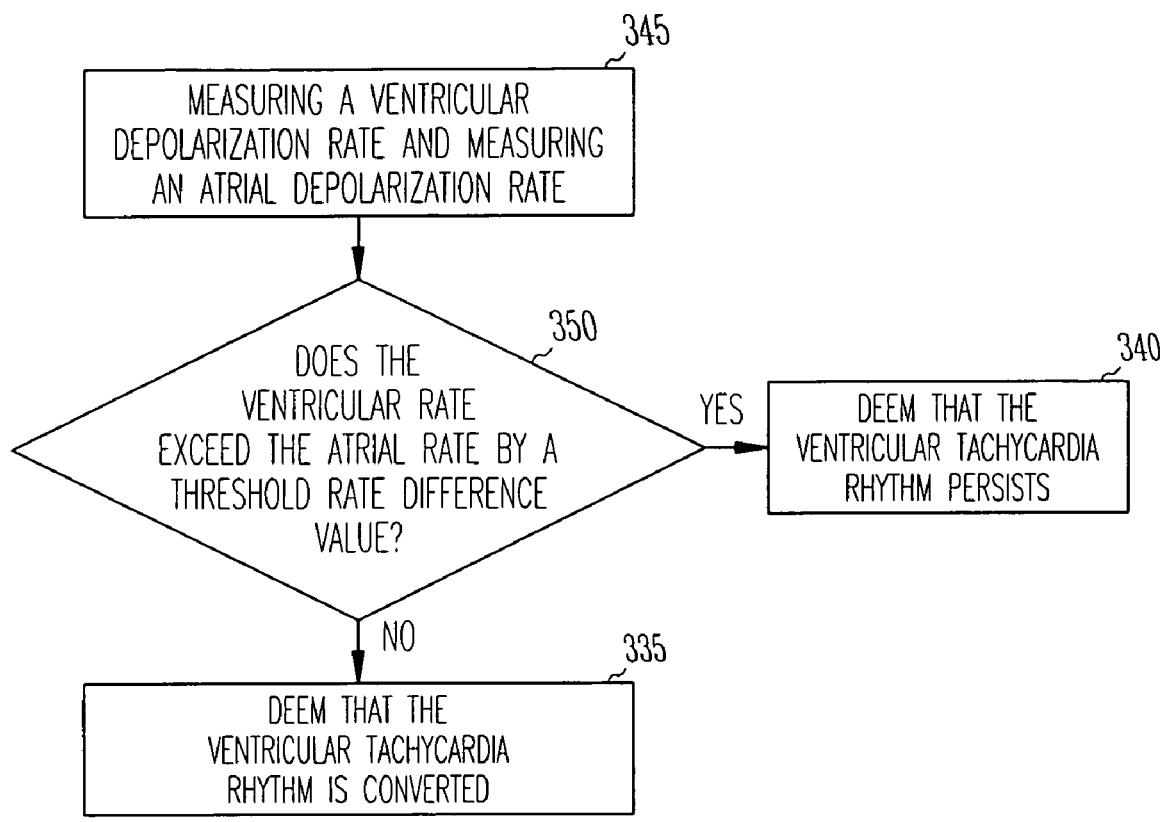

Yet another embodiment of a method 300 includes the additional steps in FIG. 3B. At 345, both a ventricular depolarization rate and an atrial depolarization rate are measured for the patient. If at 330, a fraction of the intervals between the ventricular depolarizations are not shorter than a threshold interval value, then at 350, if the ventricular rate exceeds the atrial rate by a threshold rate difference value then at 340 it is deemed that the ventricular tachycardia heart rhythm persists, otherwise, at 335 it is deemed that the ventricular tachycardia rhythm is converted.

An embodiment of the redetection method that includes the additional steps shown in FIG. 3B was applied to the database containing the post-ATP episodes. For the embodiment of the method applied, the threshold rate difference was ten bpm. The resulting sensitivities and specificities determined while varying the redetection duration time are indicated below in Table 2.

TABLE 2

Redetection Specificity and Sensitivity Results with Rate Check

| Redetection Duration Time (sec) | Sensitivity (%) | Specificity (%) |
|---|---|---|
| 5 | 100 | 88.6 |
| 4.5 | 100 | 87.5 |
| 4 | 100 | 86.4 |
| 3.5 | 100 | 84.1 |
| 3 | 100 | 78.4 |

The results show that the sensitivity of detecting a ventricular tachycardia improved using the steps in FIG. 3B of checking the difference between the ventricular and atrial rate at a cost of slightly lower specificity in detecting that a tachycardia was converted to regular heart rhythm.

Figure 4:
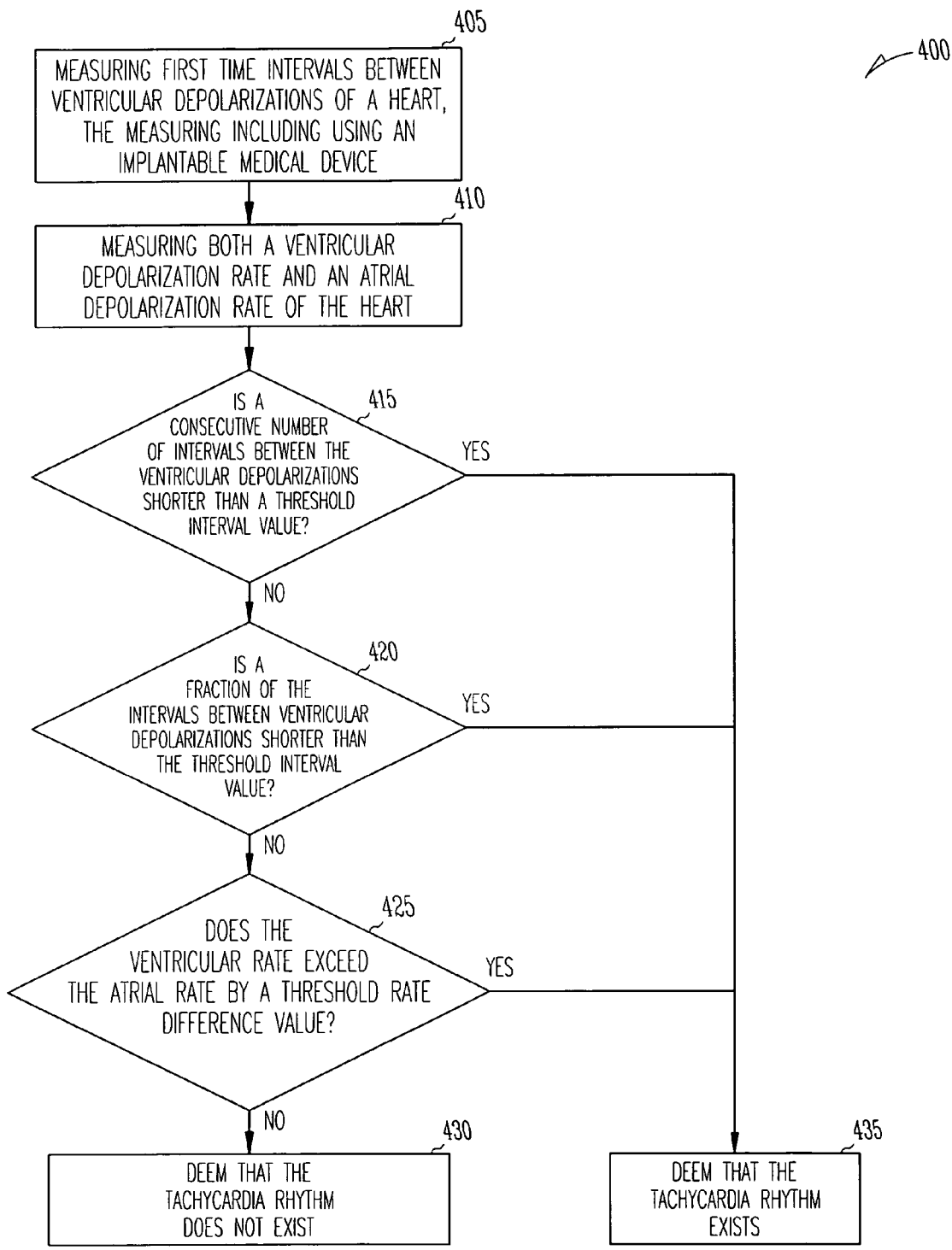
FIG. 4 is a block diagram illustrating a method of detecting ventricular tachycardia heart rhythm.

FIG. 4 shows an embodiment of a method 400 of detecting ventricular tachycardia heart rhythm. At 405, first time intervals between ventricular depolarizations of a heart are measured using an IMD. At 410, both a ventricular depolarization rate and an atrial depolarization rate of the heart are measured. At 415, if a consecutive number of intervals between the ventricular depolarizations are shorter than a threshold interval value, then at 435 it is deemed that a ventricular tachycardia rhythm exists. Otherwise at 420, if a fraction of the intervals between the ventricular depolarizations are shorter than the threshold interval value, then at 435 it is deemed that the ventricular tachycardia heart rhythm exists. Otherwise at 425, if the ventricular rate exceeds the atrial rate by a threshold rate difference value, then at 435 it is deemed that the ventricular tachycardia heart rhythm exists. Otherwise at 430, it is deemed that the ventricular tachycardia heart rhythm does not exist.

In another embodiment, the method further includes providing therapy to the heart if the ventricular tachycardia heart rhythm is deemed to exist. In yet another embodiment, the therapy includes providing anti-tachycardia pacing (ATP) therapy. In yet a further embodiment, after providing ATP therapy, the method further includes waiting a timed duration after the ATP therapy ends, measuring second time intervals and using any of the ventricular tachyarrhythmia redetection methods discussed previously to determine if the tachyarrhythmia persists.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method comprising:
   detecting a ventricular tachycardia heart rhythm in a patient using an implantable medical device (IMD);
   providing anti-tachycardia pacing (ATP) therapy to the patient in response to the ventricular tachycardia heart rhythm;
   in response to the ATP therapy ending, determining an efficacy of the ATP therapy using the IMD by:
   waiting a first time duration after the ATP therapy ends during which time sensed ventricular depolarizations are ignored, wherein the first time duration exceeds first and second tachycardia detection threshold interval values;
   establishing a redetection time duration after the first time duration has elapsed;
   monitoring the ventricular depolarizations during the redetection duration, wherein the monitoring includes:
   measuring time intervals between the ventricular depolarizations;
   determining if a specified consecutive number of the intervals between the ventricular depolarizations are shorter than the first tachycardia detection threshold interval value, and, if so, then deeming that the ventricular tachycardia rhythm persists; and
   concurrently determining if, during the same redetection duration, a predetermined fraction of the consecutive intervals between the ventricular depolarizations are shorter than the second tachycardia detection threshold interval value that is different than the first threshold interval value, and, if so, then deeming that the ventricular tachycardia heart rhythm persists, wherein the fraction is less than 100%, otherwise,
   providing an indication of efficacy of the ATP therapy indicating whether the ventricular tachycardia rhythm is converted.

2. The method if claim 1, wherein the monitoring the ventricular depolarizations includes measuring a ventricular depolarization rate, wherein the method further includes measuring an atrial depolarization rate for the patient, and wherein the deeming that the ventricular tachycardia rhythm is converted, includes first performing an additional test, wherein the additional test includes:
   if the ventricular rate exceeds the atrial rate by a threshold rate difference value then deeming that the ventricular tachycardia heart rhythm persists, otherwise,
   deeming that the ventricular tachycardia rhythm is converted.

3. The method of claim 1, wherein the monitoring the ventricular depolarizations after the first time duration includes monitoring the ventricular depolarizations during a second time duration, and wherein the deeming that the ventricular tachycardia rhythm is converted includes deeming the ventricular tachycardia rhythm is converted if the second time duration elapses without deeming that the ventricular tachycardia rhythm persists.

4. The method of claim 1, wherein the monitoring the ventricular depolarizations includes monitoring the ventricular depolarizations using an implantable medical device.

5. The method of claim 1, wherein the method further includes providing anti-tachycardia therapy if deeming that the ventricular tachycardia heart rhythm persists.

6. The method of claim 5, wherein the providing the anti-tachycardia therapy includes providing defibrillation therapy.

7. The method of claim 5, wherein the providing the anti-tachycardia therapy includes providing ATP therapy.

8. The method of claim 5, wherein the providing the anti-tachycardia therapy includes providing drug therapy.

9. A system, comprising:
   an implantable medical device comprising:
   a signal sensing circuit coupled to at least one electrode, the electrode located to sense a cardiac signal of a ventricle of a heart of a patient;
   a therapy circuit; and
   a controller coupled to the signal sensing circuit and the therapy circuit, wherein the controller:
   detects a ventricular tachycardia heart rhythm from the cardiac signal;
   initiates anti-tachycardia pacing (ATP) therapy to the patient in response to the ventricular tachycardia heart rhythm and, in response to the ATP therapy ending and in order to determine an efficacy of the APT therapy:
   waits a first time duration after the ATP therapy ends during which time sensed ventricular depolarizations are ignored, wherein the first time duration exceeds first and second tachycardia detection threshold interval values;
   initiates a redetection time duration after the first time duration expires;
   measures time intervals between ventricular depolarizations after providing ATP therapy and during the redetection time duration;
   compares the intervals to the first tachycardia detection threshold interval value; and
   determines if a consecutive number of the intervals are shorter than the first threshold interval value, and, if so, then deems that the ventricular tachycardia rhythm persists, and concurrently determines if, during the same redetection time duration, a predetermined fraction of the consecutive intervals are shorter than the second tachycardia detection threshold interval value that is different than the first threshold interval value, and if so, then deems that the ventricular tachycardia heart rhythm persists, wherein the predetermined fraction is less than 100%, otherwise provides an indication of efficacy of the ATP therapy indicating whether the ventricular tachycardia heart rhythm is converted.

10. The system of claim 9, wherein the implantable medical device further includes:

an atrial signal sensing circuit coupled to at least one second electrode and the controller, the at least one second electrode located to sense a cardiac signal of an atrium of the heart; and wherein the controller is further operable in measuring both a ventricular depolarization rate and an atrial depolarization rate for the patient, and if the ventricular depolarization rate exceeds the atrial depolarization rate by a threshold rate difference value then deem that the ventricular tachycardia heart rhythm persists, otherwise deem that the ventricular tachycardia rhythm is converted.

11. The system of claim 9, wherein the controller is operable to time a programmable wait duration after providing ATP therapy and before measuring time intervals to determine whether ventricular tachycardia persists after the providing ATP therapy.

12. The system of claim 9, wherein the controller is operable to time a programmable redetection duration during which the controller measures the time intervals between the ventricular depolarizations, and wherein the controller deems the ventricular tachycardia heart rhythm is converted if the redetection duration elapses without deeming that the ventricular tachycardia heart rhythm persisted.

13. The system of claim 9, wherein the therapy circuit includes a defibrillation therapy circuit and the implantable medical device provides defibrillation therapy if the ventricular tachycardia heart rhythm is deemed to persist.

14. The system of claim 13, wherein the implantable medical device provides ATP therapy while the defibrillation therapy circuit is charging, and wherein the controller is operable to determine if the ventricular tachycardia rhythm is converted while the defibrillation therapy circuit is charging.

15. The system of claim 14, wherein the controller is operable to abort the charging of the defibrillation therapy circuit if the ventricular tachycardia rhythm is deemed converted.

16. The system of claim 9, wherein the implantable medical device provides ATP therapy if the ventricular tachycardia heart rhythm is deemed to persist.

17. The system of claim 9, wherein the therapy circuit includes a drug therapy circuit and the implantable medical device provides drug therapy if the ventricular tachycardia heart rhythm is deemed to persist.

18. The system of claim 9, wherein the implantable medical device further includes a memory coupled to the controller, wherein the controller is operable to store patient information about whether a ventricular tachycardia heart rhythm was converted.

19. The system of claim 9, wherein the system further includes an external device operable to communicate with the implantable device, wherein the external device includes a display to display patient information about at least one of a redetection duration and whether a ventricular tachycardia heart rhythm was converted.

20. The system of claim 19, wherein the patient information includes a histogram of patient information about at least one of a redetection duration and whether a ventricular tachycardia heart rhythm was converted.

21. The system of claim 19, wherein the external device is operable to communicate with a computer network.

22. A method comprising:

measuring first time intervals between ventricular depolarizations of a heart during a tachyarrhythmia detection time duration, the measuring including using an implantable medical device (IMD);

measuring both a ventricular depolarization rate and an atrial depolarization rate of the heart;

determining if a specified consecutive number of intervals between the ventricular depolarizations are shorter than a first tachycardia detection threshold interval value and, if so, then deeming that a ventricular tachycardia rhythm exists;

concurrently determining if, during the same tachyarrhythmia detection time duration, a predetermined fraction of the consecutive intervals between the ventricular depolarizations are shorter than a second tachycardia detection threshold interval value that is different than the first threshold interval value, and, if so, then deeming that the ventricular tachycardia heart rhythm exists, wherein the fraction is less than 100%; and concurrently determining if, during the same tachyarrhythmia detection time duration, the ventricular rate exceeds the atrial rate by a threshold rate difference value and, if so, then deeming that the ventricular tachycardia heart rhythm exists, otherwise deeming that the ventricular tachycardia heart rhythm does not exist;

initiating ATP therapy if deeming that the ventricular tachycardia heart rhythm exists;

in response to the ATP therapy ending, determining an efficacy of the ATP therapy using the IMD by:

waiting a first time duration after the ATP therapy ends, wherein the first time duration exceeds both the first and second tachycardia detection threshold interval values, and wherein during the first time duration any sensed ventricular depolarizations are ignored; and initiating a tachyarrhythmia redetection time period after the first time duration elapses; and providing an indication of efficacy of the ATP therapy indicating whether the ventricular tachycardia is converted.

23. The method of claim 22, wherein the method further includes providing therapy to the heart if the ventricular tachycardia heart rhythm is deemed to exist.

24. The method of claim 23, wherein providing therapy to the heart includes providing anti-tachycardia pacing (ATP) therapy.

25. The method of claim 24, wherein the method further includes:

during the tachyarrhythmia redetection time period, measuring second time intervals between ventricular depolarizations, and also measuring both a second ventricular depolarization rate and a second atrial depolarization rate and, during the tachyarrhythmia redetection time period:

determining if a consecutive number of second intervals between ventricular depolarizations are shorter than the first tachyarrhythmia detection threshold interval value, and, if so, then deeming that the ventricular tachycardia rhythm persists, concurrently determining if, during the same tachyarrhythmia redetection time period, a predetermined fraction of the second intervals between ventricular depolarizations are shorter than the second tachyarrhythmia detection threshold interval value, and, if so, then deeming that the ventricular tachycardia heart rhythm persists, and concurrently determining if, during the same tachyarrhythmia redetection time period, the second ventricular rate exceeds the second atrial rate by a threshold rate difference value and, if so, then deeming that the ventricular tachycardia heart rhythm persists, otherwise deeming that the ventricular tachycardia heart rhythm is converted.

* * * * *

UNITED STATES PATENT AND TRADEMARK OFFICE
CERTIFICATE OF CORRECTION

PATENT NO. : 7,616,994 B2 Page 1 of 1
APPLICATION NO. : 10/852080
DATED : November 10, 2009
INVENTOR(S) : Dan Li It is certified that error appears in the above-identified patent and that said Letters Patent is hereby corrected as shown below:

In column 8, line 4, in Claim 2, delete "if claim" and insert -- of claim --, therefor.

In column 8, line 51, in Claim 9, delete "APT" and insert -- ATP --, therefor.

Signed and Sealed this

Twenty-sixth Day of January, 2010

David J. Kappos
*Director of the United States Patent and Trademark Office*